United States Patent
Ugolnikov et al.

(10) Patent No.: US 10,202,471 B2
(45) Date of Patent: *Feb. 12, 2019

(54) 1,3-DIPOLAR COMPOUND BEARING AN IMIDAZOLE FUNCTIONAL GROUP

(71) Applicants: COMPAGNIE GENERALE DES ETABLISSEMENTS MICHELIN, Clermont-Ferrand (FR); Michelin Recherche et Technique S.A., Granges-Paccot (CH)

(72) Inventors: Oleg Ugolnikov, Clermont-Ferrand (FR); Sergey Ivanov, Clermont-Ferrand (FR); Claire Rannoux, Clermont-Ferrand (FR); Anne-Frédérique Salit, Clermont-Ferrand (FR); Sophie Gander, Clermont-Ferrand (FR); Anne-Lise Thuilliez, Clermont-Ferrand (FR)

(73) Assignee: Compagnie Generale Des Etablissments Michelin, Clermont-Ferrand (FR)

( * ) Notice: Subject to any disclaimer, the term of this patent is extended or adjusted under 35 U.S.C. 154(b) by 50 days.

This patent is subject to a terminal disclaimer.

(21) Appl. No.: 15/031,337

(22) PCT Filed: Oct. 24, 2014

(86) PCT No.: PCT/EP2014/072838
§ 371 (c)(1),
(2) Date: Apr. 22, 2016

(87) PCT Pub. No.: WO2015/059269
PCT Pub. Date: Apr. 30, 2015

(65) Prior Publication Data
US 2016/0251456 A1  Sep. 1, 2016

(30) Foreign Application Priority Data
Oct. 25, 2013  (FR) .................... 13 60413

(51) Int. Cl.
*C07D 233/61*  (2006.01)
*C08F 8/30*  (2006.01)
*C08C 19/22*  (2006.01)

(52) U.S. Cl.
CPC .............. *C08F 8/30* (2013.01); *C07D 233/61* (2013.01); *C08C 19/22* (2013.01)

(58) Field of Classification Search
CPC ......... C07D 233/61; C08C 19/22; C08F 8/30; C08K 3/36; C08K 3/04; C08K 5/3447; C08K 5/3445; B60C 1/00; B60C 11/00
See application file for complete search history.

(56) References Cited

U.S. PATENT DOCUMENTS

| | | | |
|---|---|---|---|
| 4,803,282 A | 2/1989 | St. Georgiev et al. | 548/336 |
| 5,140,055 A | 8/1992 | Hirata et al. | 524/93 |
| 5,185,324 A | 2/1993 | Ruger et al. | 514/18 |
| 5,346,962 A | 9/1994 | Hergenrother et al. | 525/281 |
| 5,717,022 A | 2/1998 | Beckmann et al. | |
| 6,034,250 A | 3/2000 | Goldstein et al. | 548/336.1 |
| 6,194,461 B1 | 2/2001 | Ikeda et al. | 514/579 |
| 6,774,255 B1 | 8/2004 | Tardivat et al. | 556/427 |
| 7,186,845 B2 | 3/2007 | Fukushima et al. | 548/257 |
| 7,199,175 B2 | 4/2007 | Vasseur | 524/492 |
| 7,250,463 B2 | 7/2007 | Durel et al. | 524/492 |
| 7,300,970 B2 | 11/2007 | Durel et al. | 524/493 |
| 7,488,768 B2 | 2/2009 | Tardivat et al. | 524/262 |
| 7,491,767 B2 | 2/2009 | Durel et al. | 524/493 |
| 7,825,183 B2 | 11/2010 | Robert et al. | 524/476 |
| 7,834,074 B2 | 11/2010 | Brunelet et al. | 524/318 |
| 7,882,874 B2 | 2/2011 | Robert et al. | 152/209.1 |
| 7,900,667 B2 | 3/2011 | Vasseur | 152/209.1 |
| 8,278,451 B2 | 10/2012 | Becker et al. | 546/112 |
| 8,324,310 B2 | 12/2012 | Robert et al. | 524/518 |
| 8,492,475 B2 | 7/2013 | Araujo Da Silva et al. | 524/552 |
| 9,010,393 B2 | 4/2015 | Araujo Da Silva et al. | 524/575.5 |
| 9,394,434 B2 | 7/2016 | Araujo da Silva et al. | C08L 9/06 |
| 2003/0212185 A1 | 11/2003 | Vasseur | 524/492 |
| 2004/0051210 A1 | 3/2004 | Tardivat et al. | 264/349 |
| 2005/0004297 A1 | 1/2005 | Durel et al. | 524/493 |
| 2005/0016650 A1 | 1/2005 | Durel et al. | 152/209.1 |
| 2005/0016651 A1 | 1/2005 | Durel et al. | 152/209.1 |
| 2007/0112120 A1 | 5/2007 | Vasseur | 524/492 |
| 2008/0009564 A1 | 1/2008 | Robert et al. | 523/351 |

(Continued)

FOREIGN PATENT DOCUMENTS

CN  101580558 A  11/2009
CN  102985444 A  3/2013
(Continued)

OTHER PUBLICATIONS

B. Cavalleri, et al., "Synthesis and Biological Activity of Some Vinyl-Substituted 2-Nitroimidazoles," J. Med. Chem., vol. 20, No. 5, pp. 656-660 (1977).

(Continued)

*Primary Examiner* — Irina S Zemel
*Assistant Examiner* — Jeffrey S Lenihan
(74) *Attorney, Agent, or Firm* — Venable LLP

(57) ABSTRACT

In a 1,3-dipolar compound of formula Q-A-B, Q comprises a dipole containing at least and preferably one nitrogen atom, A, which is preferably divalent, is an atom or a group of atoms connecting Q to B, and B comprises an imidazole ring. An unsaturated polymer modified by grafting the 1,3-dipolar compound is also disclosed.

20 Claims, No Drawings

(56) References Cited

U.S. PATENT DOCUMENTS

| | | | |
|---|---|---|---|
| 2008/0156404 A1 | 7/2008 | Brunelet et al. | 152/209.1 |
| 2009/0186961 A1 | 7/2009 | Araujo Da Silva et al. | 523/150 |
| 2009/0209709 A1 | 8/2009 | Araujo Da Silva et al. | 525/333.1 |
| 2009/0234066 A1 | 9/2009 | Araujo Da Silva et al. | 524/571 |
| 2009/0286900 A1 | 11/2009 | Ichikawa et al. | 522/113 |
| 2009/0292063 A1 | 11/2009 | Robert et al. | 524/518 |
| 2010/0204359 A1 | 8/2010 | Robert et al. | 523/157 |
| 2011/0152458 A1 | 6/2011 | Araujo Da Silva et al. | 525/102 |
| 2012/0225233 A1 | 9/2012 | Guy et al. | 428/36.9 |
| 2012/0245270 A1 | 9/2012 | Blanchard et al. | 524/388 |
| 2013/0123418 A1 | 5/2013 | Araujo Da Silva et al. | 524/575 |
| 2013/0131279 A1 | 5/2013 | Araujo Da Silva et al. | 525/333.1 |
| 2013/0331475 A1 | 12/2013 | Ichikawa et al. | C08C 19/22 |
| 2015/0322234 A1 | 11/2015 | Fleury et al. | C08K 3/36 |
| 2016/0263943 A1 | 9/2016 | Gander et al. | B60C 1/0016 |
| 2016/0264753 A1 | 9/2016 | Salit et al. | C08K 3/36 |

FOREIGN PATENT DOCUMENTS

| | | |
|---|---|---|
| EP | 0 257 289 A2 | 3/1988 |
| EP | 0 257 391 A2 | 3/1988 |
| EP | 0 310 061 A1 | 4/1989 |
| EP | 0 373 549 A2 | 6/1990 |
| EP | 0 945 426 A1 | 9/1999 |
| EP | 0 967 207 A1 | 12/1999 |
| FR | 2 946 050 A1 | 12/2010 |
| JP | 2012-082265 A | 4/2012 |
| JP | 2013-087182 A | 5/2013 |
| JP | 2015-44929 A | 3/2015 |
| WO | 96/37547 | 11/1996 |
| WO | 99/28380 | 6/1999 |
| WO | 02/10269 A2 | 2/2002 |
| WO | 02/30939 A1 | 4/2002 |
| WO | 02/31041 A1 | 4/2002 |
| WO | 03/002648 A1 | 1/2003 |
| WO | 03/002649 A1 | 1/2003 |
| WO | 03/016387 A1 | 2/2003 |
| WO | 2005/087859 A1 | 9/2005 |
| WO | 2006/045088 A1 | 4/2006 |
| WO | 2006/061064 A1 | 6/2006 |
| WO | 2006/125532 A1 | 11/2006 |
| WO | 2006/125533 A1 | 11/2006 |
| WO | 2006/125534 A1 | 11/2006 |
| WO | 2007/017060 A1 | 2/2007 |
| WO | WO 2008/002614 A2 | 1/2008 |
| WO | 2011/045131 A1 | 4/2011 |
| WO | 2012/007442 A1 | 1/2012 |
| WO | WO 2012/007441 A1 | 1/2012 |

OTHER PUBLICATIONS

S. Brunauer, et al., "Adsorption of Gases in Multimolecular Layers", J. Am. Chem. Soc., vol. 60, pp. 309-319 (1938).

I.G. Zenkevich, et al., "Identification of Alyklarene Chloromethylation Products Using Gas-Chromatographic Retention Indices", Russian Journal of General Chemistry, vol. 77, No. 4, pp. 611-619 (2007)(English translation of Zhurnal Obshchei Khimii, vol. 77, No. 4, pp. 653-662(2007)).

A. P. Yakubov, et al., "Synthesis of Sterically Hindered Aromatic Aldehydes", M. M., Bulletin of the Academy of Sciences of the USSR, Division of Chemical Science, vol. 40, No. 7.2, pp. 1427-1432 (1991)(English Translation of Izvestiya Akademii Nauk SSSR, Seriya Khimicheskaya, No. 7, pp. 1609-1615 (1991)).

Office Action issued in counterpart Japanese Patent Application No. 2016-526223, dated Oct. 18, 2018 (6 pages).

1,3-DIPOLAR COMPOUND BEARING AN IMIDAZOLE FUNCTIONAL GROUP

FIELD OF THE INVENTION

The field of the present invention is that of modifying agents intended to functionalize unsaturated polymers along the polymer chain.

RELATED ART

Modifying the chemical structure of a polymer generally impacts the chemical and physical properties of the polymer, and also the properties of the compositions containing it. Modifying the structure of a polymer, such as the functionalization of a polymer, is particularly sought for when it is desired to bring together a polymer and a filler in a composition. Chemically modifying a polymer can improve the dispersion of the filler in the polymer and can thus make it possible to obtain a more homogeneous material. In the case of certain fillers, such as carbon black or silica, a better dispersion of the filler will generally be reflected by a fall in hysteresis of the composition. Such a property is sought for, in particular in rubber compositions intended, for example, for tyre applications. This fall in hysteresis is often accompanied by a fall in the stiffness in the cured state of the composition, which can render the composition unsuitable for the use which it is desired to make of it. There thus exists a need to find modifying agents which make it possible both to functionalize a polymer and to modify this hysteresis/stiffness in the cured state compromise of a composition comprising a polymer and a filler.

The chemical reactions for modifying an unsaturated polymer include the reactions for grafting a compound. Known compounds for being grafted to an unsaturated polymer are, for example, 1,3-dipolar compounds, such as described in Patent Applications WO 2006/045088 and WO 2012/007441. The first patent application describes compounds which make possible the grafting of an oxazoline, thiazoline, alkoxysilane or allyltin functional group. The second describes compounds which make possible the grafting of nitrogen-based associative functional groups. However, neither of these patent applications describes 1,3-dipolar compounds bearing an imidazole ring, or the grafting of an imidazole ring to an unsaturated polymer by reaction of these 1,3-dipolar compounds with the aim of modifying the hysteresis/stiffness in the cured state compromise of a composition comprising the polymer in the presence of a filler.

BRIEF DESCRIPTION OF EMBODIMENTS OF THE INVENTION

Thus, a first subject-matter of the invention is a 1,3-dipolar compound corresponding to the formula (I):

$$Q\text{-}A\text{-}B \qquad (I)$$

in which:
Q comprises a dipole containing at least and preferably one nitrogen atom,
A, which is preferably divalent, is an atom or a group of atoms connecting Q to B,
B comprises an imidazole ring corresponding to the formula (II):

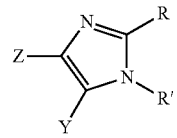

in which:
three of the four symbols Z, Y, R and R', which are identical or different, each represent an atom or a group of atoms, it being possible for Z and Y to form, together with the carbon atoms to which they are attached, a ring,
and the fourth symbol Z, Y, R or R' denotes a direct attachment to A.

The invention also relates to a process for modifying an unsaturated polymer, which process comprises the reaction of a 1,3-dipolar compound in accordance with the invention with at least one and preferably several unsaturations of the unsaturated polymer.

The invention also relates to a polymer which is capable of being obtained by the process in accordance with the invention.

I. DETAILED DESCRIPTION OF THE INVENTION

In the present description, unless expressly indicated otherwise, all the percentages (%) shown are % by weight. The abbreviation "phr" means parts by weight per hundred parts of elastomer (of the total of the elastomers, if several elastomers are present).

Furthermore, any interval of values denoted by the expression "between a and b" represents the range of values greater than "a" and lower than "b" (that is to say, limits a and b excluded), whereas any interval of values denoted by the expression "from a to b" means the range of values extending from "a" up to "b" (that is to say, including the strict limits a and b).

The term "1,3-dipolar compound" is understood according to the definition given by the IUPAC.

The 1,3-dipolar compound corresponds to the formula (I):

$$Q\text{-}A\text{-}B \qquad (I)$$

in which:
Q comprises a dipole containing at least and preferably one nitrogen atom,
A, which is preferably divalent, is an atom or a group of atoms connecting Q to B,
B comprises an imidazole ring corresponding to the formula (II):

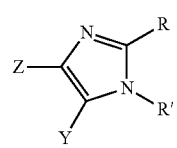

in which:
three of the four symbols Z, Y, R and R', which are identical or different, each represent an atom or a group of atoms, it being possible for Z and Y to form, together with the carbon atoms to which they are attached, a ring (of course, when neither Z nor Y denotes the 4$^{th}$ symbol), and just the fourth symbol denotes a direct attachment to A.

According to a first alternative form of the invention, R denotes a direct attachment to A, in which case R is the 4$^{th}$ symbol.

According to this alternative form, R' can be a hydrogen atom or a carbon-based group which can contain at least one heteroatom.

According to a preferred embodiment of this alternative form, R' represents a carbon-based group containing from 1 to 20 carbon atoms, preferably an aliphatic group, more preferably an alkyl group which preferably contains from 1 to 12 carbon atoms.

According to a second alternative form of the invention, R' denotes a direct attachment to A, in which case R' is the 4$^{th}$ symbol.

According to the first or the second alternative form, Z and Y can each be a hydrogen atom.

According to another embodiment of the first alternative form or of the second alternative form, Z and Y form, together with the carbon atoms to which they are attached, a ring. The ring formed by Z, Y and the atoms to which Z and Y are attached may or may not be substituted and can comprise at least one heteroatom. Z and Y can form, with the two carbon atoms to which they are attached, an aromatic nucleus. In this case, the imidazole ring can be a substituted or unsubstituted benzimidazole.

According to a third alternative form of the invention, of course when Y and Z do not form, together with the carbon atoms to which they are attached, a ring, Y or Z denotes a direct attachment to A, in which case Y or Z is the 4$^{th}$ symbol.

According to a specific embodiment of the second or of the third alternative form of the invention, R represents a hydrogen atom or a carbon-based group which can contain at least one heteroatom.

According to this specific embodiment of the second alternative form or of the third alternative form of the invention, R can be a group of 1 to 20 carbon atoms, preferably an aliphatic group, more preferably an alkyl group preferably containing from 1 to 12 carbon atoms, more preferably still a methyl.

A can be a group containing up to 20 carbon atoms, which group can contain at least one heteroatom. A can be an aliphatic or aromatic group.

When A is an aliphatic group, A preferably contains from 1 to 20 carbon atoms, more preferably from 1 to 12 carbon atoms, more preferably still from 1 to 6 carbon atoms and very particularly from 1 to 3 carbon atoms. When A is an aromatic group, A preferably contains from 6 to 20 carbon atoms, more preferably from 6 to 12 carbon atoms.

Particularly suitable as divalent group A is an alkylene group containing from 1 to 20 carbon atoms, preferably from 1 to 12 carbon atoms, more preferably from 1 to 6 carbon atoms and more preferably still from 1 to 3 carbon atoms. Mention may be made, as divalent group A containing from 1 to 3 carbon atoms which is suitable, of the methylene group.

An arylene group preferably containing from 6 to 20 carbon atoms, more preferably from 6 to 12 carbon atoms, may also be suitable as divalent group A.

Very particularly suitable as 1,3-dipolar compounds are the compounds selected from the group consisting of nitrile oxides, nitrile imines and nitrones, in which case Q contains a —C≡N→O, —C≡N→N— or —C═N(→O)— unit.

According to the specific embodiment of the invention where Q comprises a —C≡N→O unit, Q preferably comprises, more preferably represents, the unit corresponding to the formula (III) in which four of the five symbols $R_1$ to $R_5$, which are identical or different, are each an atom or a group of atoms and the fifth symbol denotes a direct attachment to A, it being known that $R_1$ and $R_5$ are both other than H. The four of the five symbols $R_1$ to $R_5$ can be aliphatic or aromatic groups. The aliphatic groups can contain from 1 to 20 carbon atoms, preferably from 1 to 12 carbon atoms, more preferably from 1 to 6 carbon atoms and more preferably still from 1 to 3 carbon atoms. The aromatic groups can contain from 6 to 20 carbon atoms and preferably from 6 to 12 carbon atoms.

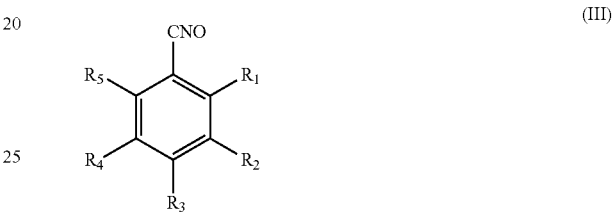

(III)

$R_1$, $R_3$ and $R_5$ are preferably each an alkyl group of 1 to 6 carbon atoms, more preferably of 1 to 3 carbon atoms, and more preferably still a methyl or ethyl group.

According to an alternative form of this specific embodiment of the invention, $R_1$, $R_3$ and $R_5$ are identical. According to this alternative form where they are identical, $R_1$, $R_3$ and $R_5$ are preferably each an alkyl group of 1 to 6 carbon atoms, more preferably of 1 to 3 carbon atoms, and more preferably still a methyl or ethyl group.

More preferably, the 1,3-dipolar compound is the compound 2,4,6-trimethyl-3-((2-methyl-1H-imidazol-1-yl)methyl)benzonitrile oxide, corresponding to the formula (IIIa), or the compound 2,4,6-triethyl-3-((2-methyl-1H-imidazol-1-yl)methyl)benzonitrile oxide, corresponding to the formula (IIIb):

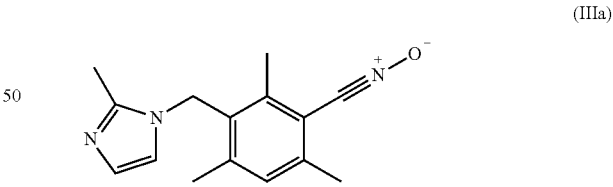

(IIIa)

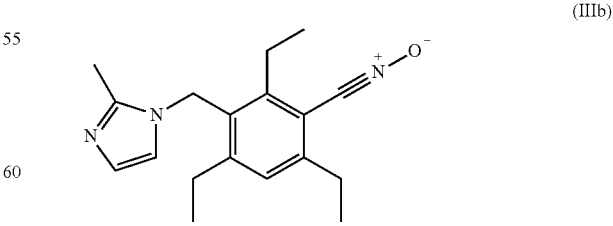

(IIIb)

According to the specific embodiment of the invention where Q comprises a —C═N(→O)— unit, Q preferably comprises, more preferably represents, the unit corresponding to the formula (IV) or (V):

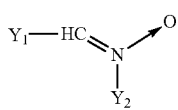 (IV)

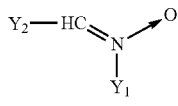 (V)

in which:
- $Y_1$ is an aliphatic group, preferably an alkyl group preferably containing from 1 to 12 carbon atoms, or an aromatic group containing from 6 to 20 carbon atoms, preferably an alkylaryl group, more preferably a phenyl or tolyl group,
- and $Y_2$, comprising a direct attachment to A, is an aliphatic group, preferably an alkylene group preferably containing from 1 to 12 carbon atoms, or an aromatic group preferably containing from 6 to 20 carbon atoms and comprising, on its benzene nucleus, the direct attachment to A.

The direct attachment of the benzene nucleus of $Y_2$ to A amounts to saying that A is a substituent of the benzene nucleus of $Y_2$.

According to this specific embodiment of the invention, the 1,3-dipolar compound is the compound of formula (IVa), (IVb), (Va) or (Vb):

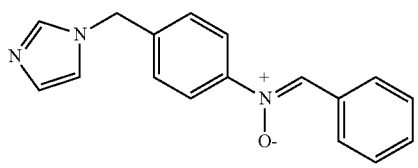 (IVa)

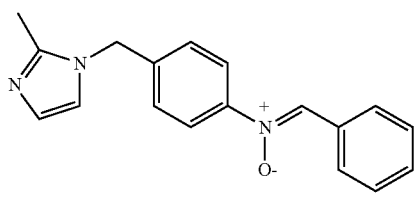 (IVb)

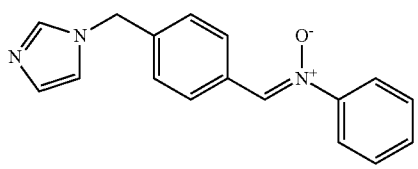 (Va)

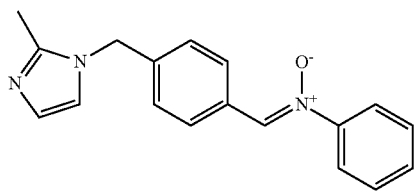 (Vb)

The process, which is another subject-matter of the invention, comprises the reaction of the 1,3-dipolar compound described above with at least one and preferably several unsaturations of an unsaturated polymer. Several unsaturations is understood to mean at least two unsaturations.

The 1,3-dipolar compound can be used to modify an unsaturated polymer by a grafting reaction of the 1,3-dipolar compound with at least one and preferably several unsaturations of the unsaturated polymer.

According to a preferred embodiment of the invention, the unsaturations of the polymer are carbon-carbon bonds, preferably carbon-carbon double bonds.

The grafting of the 1,3-dipolar compound is carried out by [3+2]cycloaddition of the reactive group or groups of the 1,3-dipolar compound to one or more double bonds of a diene elastomer chain. The mechanism of the cycloaddition of a nitrile oxide, a nitrone and a nitrile imine can be illustrated by the following equations, in which the symbol ▫ represents any substituent:

Cycloaddition of a nitrile oxide to an unsaturation or double bond of a diene elastomer (in this instance a polyisoprene)

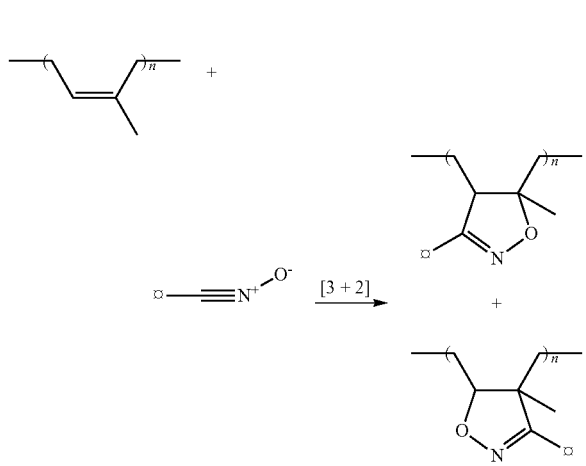

Cycloaddition of a nitrone to an unsaturation or double bond of a diene elastomer (in this instance a polyisoprene)

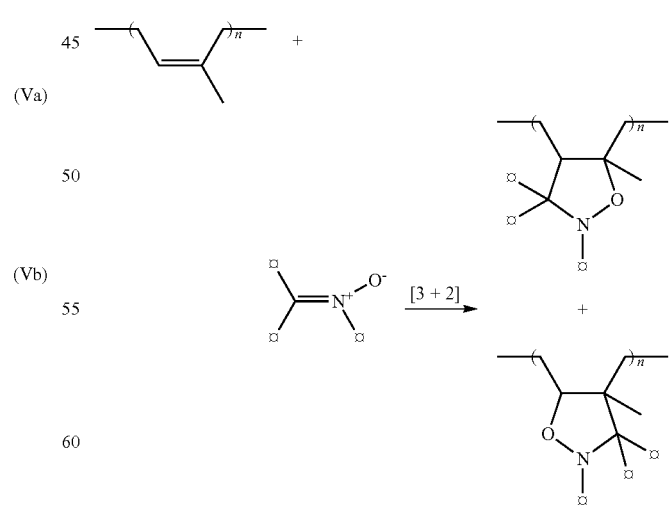

Cycloaddition of a nitrile imine to an unsaturation or double bond of a diene elastomer (in this instance a polyisoprene)

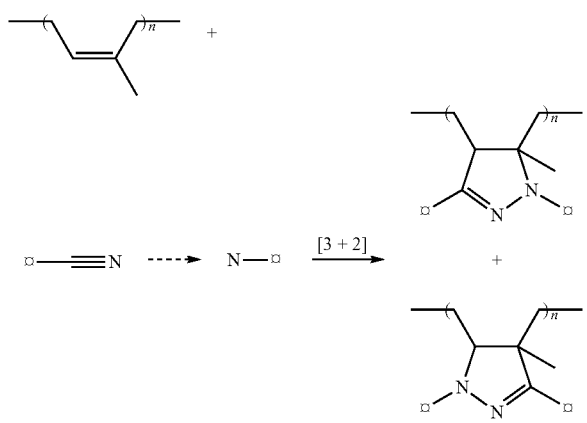

The grafting of the 1,3-dipolar compound can be carried out in bulk, for example in an internal mixer or an external mixer, such as an open mill. The grafting is then carried out either at a temperature of the external mixer or of the internal mixture of less than 60° C., followed by a stage of a grafting reaction under a press or in an oven at temperatures ranging from 80° C. to 200° C., or at a temperature of the external mixer or of the internal mixer of greater than 60° C., without subsequent heat treatment.

The grafting process can also be carried out in solution. The temperature at which the grafting is carried out is easily adjusted by a person skilled in the art from his general knowledge by taking into account the concentration of the reaction medium, the reflux temperature of the solvent, the thermal stability of the polymer and the 1,3-dipolar compound. For example, a temperature in the vicinity of 60° C. may be suitable. The polymer, thus modified, can be separated from its solution by any type of means known to a person skilled in the art and in particular by an operation of evaporation of the solvent under reduced pressure or by a steam stripping operation.

In the grafting reaction for modifying the unsaturated polymer, the 1,3-dipolar compound is reacted according to a preferred stoichiometry of between 0 and 3 molar equivalents, more preferably between 0 and 2 molar equivalents, more preferably still between 0 and 1 molar equivalent, indeed even more preferably still between 0 and 0.7 molar equivalent, of imidazole ring per 100 moles of monomer units constituting the polymer. For each of these preferred ranges, the lower limit is advantageously at least 0.1 molar equivalent of 1,3-dipolar compound. The amount of 1,3-dipolar compound used for grafting the polymer is expressed as molar equivalent of imidazole ring. For example, if the 1,3-dipolar compound contains just one imidazole ring of formula (II) as defined above, one mole of imidazole ring corresponds to one mole of 1,3-dipolar compound. If the 1,3-dipolar compound contains two imidazole rings of formula (II) as defined above, two moles of imidazole ring correspond to one mole of 1,3-dipolar compound. In the latter case, the use of the 1,3-dipolar compound according to one molar equivalent of imidazole ring corresponds to a half-mole of 1,3-dipolar compound.

Preferably, whether the grafting is carried out in solution or in bulk, the polymer is antioxidized beforehand in order to prevent possible degradation of the macrostructure of the polymer during the grafting reaction.

The unsaturated polymer to be modified exhibits at least one and preferably several unsaturations which are capable of reacting with the 1,3-dipolar compound in accordance with the invention.

The unsaturated polymer is preferably a diene polymer, more preferably a diene elastomer.

Diene polymer should be understood as meaning a polymer comprising diene monomer units, in particular 1,3-diene monomer units.

A "diene" elastomer (or without distinction rubber) should be understood, in a known way, as meaning an elastomer composed, at least in part (i.e., a homopolymer or a copolymer), of diene monomer units (monomers bearing two conjugated or non-conjugated carbon-carbon double bonds).

These diene elastomers can be classified into two categories: "essentially unsaturated" or "essentially saturated". Generally, "essentially unsaturated" is understood to mean a diene elastomer resulting at least in part from conjugated diene monomers having a content of units diene origin (conjugated dienes) which is greater than 15% (mol %); thus it is that diene elastomers such as butyl rubbers or copolymers of dienes and α-olefins of EPDM type do not come within the preceding definition and can in particular be described as "essentially saturated" diene elastomers (low or very low content, always less than 15%, of units of diene origin). In the category of "essentially unsaturated" diene elastomers, the term "highly unsaturated" diene elastomer is understood to mean in particular a diene elastomer having a content of units of diene origin (conjugated dienes) which is greater than 50%.

Given these definitions, diene elastomer capable of being used in the compositions in accordance with the invention is understood more particularly to mean:

(a)—any homopolymer of a conjugated diene monomer, in particular any homopolymer obtained by polymerization of a conjugated diene monomer having from 4 to 12 carbon atoms;

(b)—any copolymer obtained by copolymerization of one or more conjugated dienes with one another or with one or more vinylaromatic compounds having from 8 to 20 carbon atoms;

(c)—a ternary copolymer obtained by copolymerization of ethylene and of an α-olefin having from 3 to 6 carbon atoms with a non-conjugated diene monomer having from 6 to 12 carbon atoms, such as, for example, the elastomers obtained from ethylene and propylene with a non-conjugated diene monomer of the abovementioned type, such as, in particular, 1,4-hexadiene, ethylidenenorbornene or dicyclopentadiene;

(d)—a copolymer of isobutene and isoprene (butyl rubber) and also the halogenated versions, in particular chlorinated or brominated versions, of this type of copolymer.

Although it applies to any type of diene elastomer, a person skilled in the art of tyres will understand that the present invention is preferably employed with essentially unsaturated diene elastomers, in particular of the above type (a) or (b).

In the case of copolymers of the type (b), the latter comprise from 20% to 99% by weight of diene units and from 1% to 80% by weight of vinylaromatic units.

The following are suitable in particular as conjugated dienes: 1,3-butadiene, 2-methyl-1,3-butadiene, 2,3-di($C_1$-$C_5$ alkyl)-1,3-butadienes, such as, for example, 2,3-dimethyl-1,3-butadiene, 2,3-diethyl-1,3-butadiene, 2-methyl-3-ethyl-1,3-butadiene or 2-methyl-3-isopropyl-1,3-butadiene, an aryl-1,3-butadiene, 1,3-pentadiene or 2,4-hexadiene.

The following, for example, are suitable as vinylaromatic compounds: styrene, ortho-, meta- or para-methylstyrene, the "vinyltoluene" commercial mixture, para-(tert-butyl) styrene, methoxystyrenes, chlorostyrenes, vinylmesitylene, divinylbenzene or vinylnaphthalene.

Preferably, the diene elastomer is an essentially unsaturated elastomer selected from the group consisting of polybutadienes (BRs), polyisoprenes, butadiene copolymers, isoprene copolymers and the mixtures of these elastomers. Very particularly suitable as diene elastomer is a polybutadiene (BR), a copolymer of butadiene and styrene (SBR), a natural rubber (NR) or a synthetic polyisoprene (IR) preferably exhibiting a molar content of cis-1,4-bonds of greater than 90%.

Another subject-matter of the invention is the polymer which can be obtained by the process described according to any one of its embodiments.

The polymer which is a subject-matter of the invention is preferably a diene polymer, preferably a diene elastomer, more preferably an essentially unsaturated diene elastomer, more preferably still an essentially unsaturated elastomer selected from the group consisting of polybutadienes, polyisoprenes, butadiene copolymers, isoprene copolymers and the mixtures of these elastomers.

The abovementioned characteristics of the present invention, and also others, will be better understood on reading the following description of several implementational examples of the invention, given by way of illustration and without limitation.

II. IMPLEMENTATIONAL EXAMPLES OF THE INVENTION

II1.1—Measurements and Tests Used

NMR Analysis:

The structural analysis and also the determination of the molar purities of the molecules synthesized are carried out by an NMR analysis. The spectra are acquired on a Bruker Avance 3400 MHz spectrometer equipped with a 5 mm BBFO Z-grad "broad band" probe. The quantitative $^1$H NMR experiment uses a simple 30° pulse sequence and a repetition time of 3 seconds between each of the 64 acquisitions. The samples are dissolved in a deuterated solvent, deuterated dimethyl sulphoxide (DMSO), unless otherwise indicated. The deuterated solvent is also used for the lock signal. For example, calibration is carried out on the signal of the protons of the deuterated DMSO at 2.44 ppm with respect to a TMS reference at 0 ppm. The $^1$H NMR spectrum coupled with the 2D $^1$H/$^{13}$C HSQC and $^1$H/$^{13}$C HMBC experiments make possible the structural determination of the molecules (cf. tables of assignments). The molar quantifications are carried out from the quantitative 1D $^1$H NMR spectrum.

The determination of the molar content of grafted nitrile oxide compound is carried out by an NMR analysis. The spectra are acquired on a 500 MHz Bruker spectrometer equipped with a "5 mm BBFO Z-grad CryoProbe". The quantitative $^1$H NMR experiment uses a simple 30° pulse sequence and a repetition time of 5 seconds between each acquisition. The samples are dissolved in deuterated chloroform (CDCl$_3$) with the aim of obtaining a lock signal.

2D NMR experiments have made it possible to confirm the nature of the grafted unit by virtue of the chemical shifts of the carbon and proton atoms.

II.2—Synthesis of the 1,3-dipolar Compound 2,4,6-trimethyl-3-((2-methyl-1H-imidazol-1-yl)methyl) benzonitrile Oxide This compound can be prepared according to the following reaction scheme:

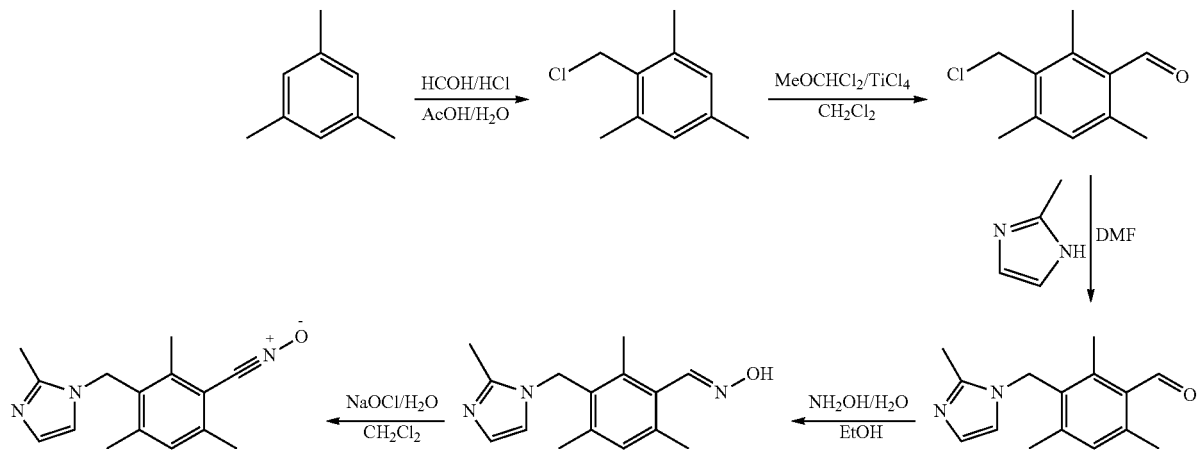

II.2-1—Synthesis of 2-(chloromethyl)-1,3,5-trimethylbenzene

This compound can be obtained according to a procedure described in the following paper: Zenkevich, I. G. and Makarov, A. A., Russian Journal of General Chemistry, Vol. 77, No. 4 (2007), pp. 611-619 (Zhurnal Obshchei Khimii, Vol. 77, No. 4 (2007), pp. 653-662).

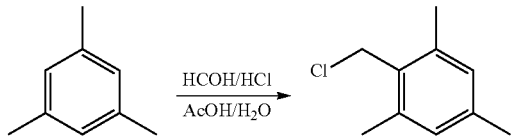

A mixture of mesitylene (100.0 g, 0.832 mol), paraformaldehyde (26.2 g, 0.874 mol) and hydrochloric acid (240 ml, 37%, 2.906 mol) in acetic acid (240 ml) is stirred and heated very slowly (1.5 hours) up to 37° C. After returning to ambient temperature, the mixture is diluted with water (1.0 l) with CH$_2$Cl$_2$ (200 ml) and the product is extracted with CH$_2$Cl$_2$ (4 times with 50 ml). The organic phases are combined, then washed with water (5 times with 100 ml) and evaporated down to 11-12 mbar (temperature of the bath=42° C.). A colourless oil (133.52 g, yield 95%) is obtained. After 15-18 hours at +4° C., the oil crystallized. The crystals are filtered off, washed with petroleum ether cooled to −18° C. (40 ml) and then dried under atmospheric pressure at ambient temperature for 3 to 5 hours. A white solid (95.9 g, yield 68%) with a melting point of 39° C. is obtained. The molar purity is greater than 96% ($^1$H NMR).

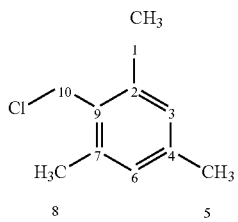

| No. | δ $^1$H (ppm) | δ $^{13}$C (ppm) |
|---|---|---|
| 1/8 | 2.27 | 18.4 |
| 2/7 | — | 136.9 |
| 3/6 | 6.81 | 128.5 |
| 4 | — | 137.4 |
| 5 | 2.15 | 20.3 |
| 9 | — | 130.5 |
| 10 | 4.69 | 41.3 |

II.2-2—Synthesis of 3-(chloromethyl)-2,4,6-trimethylbenzaldehyde

This compound can be obtained according to a procedure described in the following paper: Yakubov, A. P., Tsyganov, D. V., Belen'kii, L. I. and Krayushkin, M. M., Bulletin of the Academy of Sciences of the USSR, Division of Chemical Science (English Translation), Vol. 40, No. 7.2 (1991), pp. 1427-1432 (Izvestiya Akademii Nauk SSSR, Seriya Khimicheskaya; No. 7 (1991), pp. 1609-1615).

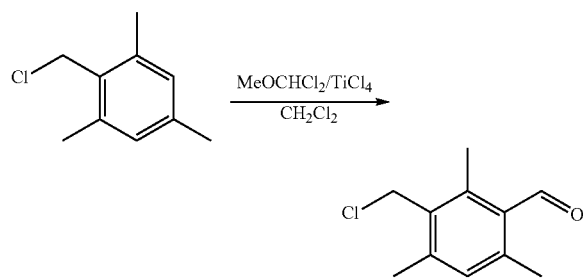

A solution of 2-(chloromethyl)-1,3,5-trimethylbenzene (20.0 g, 0.118 mol) and dichloromethyl methyl ether (27.26 g, 0.237 mol) in dichloromethane (200 ml) is added under argon over 10-12 minutes to a solution of TiCl$_4$ (90.0 g, 0.474 mol) in dichloromethane (200 ml) at 17° C. After stirring at 17-20° C. for 15-20 minutes, water (1000 ml) and ice (500 g) are added to the reaction medium. After stirring for 10-15 minutes, the organic phase is separated. The aqueous phase is extracted with CH$_2$Cl$_2$ (3 times with 75 ml). The combined organic phases are washed with water (4 times with 100 ml) and evaporated under reduced pressure to result in a solid (temperature of the bath=28° C.). The target product (22.74 g) is obtained with a yield of 97%, with a melting point of 58° C. The molar purity, estimated by $^1$H NMR, is 95 mol %.

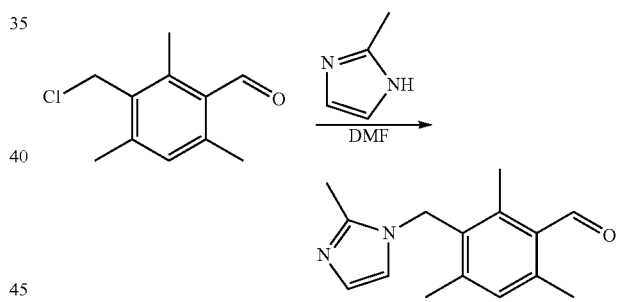

| No. | δ $^1$H (ppm) | δ $^{13}$C (ppm) |
|---|---|---|
| 1 | 4.77 | 40.6 |
| 2 | — | 132.9 |
| 3 | — | 139.5 |
| 4 | 2.51 | 14.4 |
| 5 | — | 131.4 |
| 6 | 10.43 | 194.2 |
| 7 | — | 140.1 |
| 8 | 2.41 | 19.3 |
| 9 | 6.99 | 131.2 |
| 10 | — | 142.4 |
| 11 | 2.34 | 19.8 |

II.2-3—Synthesis of 2,4,6-trimethyl-3-((2-methyl-1H-imidazol-1-yl)methyl)benzaldehyde A mixture of 3-(chloromethyl)-2,4,6-trimethylbenzaldehyde (10.0 g, 0.051 mol) and imidazole (10.44 g, 0.127 mol) in DMF (10 ml) is stirred at 80° C. for one hour. After returning to 40-50° C., the mixture is diluted with water (200 ml) and stirred for 10 minutes. The precipitate obtained is filtered off, washed on the filter with water (4 times with 25 ml) and then dried at ambient temperature. A white solid (7.92 g, yield 64%) with a melting point of 161° C. is obtained. The molar purity is 91% ($^1$H NMR).

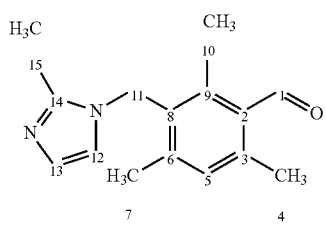

| No. | δ ¹H (ppm) | δ ¹³C (ppm) |
|---|---|---|
| 1 | 10.45 | 194.2 |
| 2 | — | 131.5 |
| 3 | — | 139.5 |
| 4 | 2.44 | 19.6 |
| 5 | 7.04 | 131.2 |
| 6 | — | 142.5 |
| 7 | 2.19 | 19.5 |
| 8 | — | 131 |
| 9 | — | 139.5 |
| 10 | 2.34 | 14.6 |
| 11 | 5.02 | 42.5 |
| 12 | 6.24 | 116.9 |
| 13 | 6.59 | 125.9 |
| 14 | — | 143.5 |
| 15 | 2.32 | 12.7 |

II.2-4—Synthesis of 2,4,6-trimethyl-3-((2-methyl-1H-imidazol-1-yl)methyl)benzaldehyde Oxime

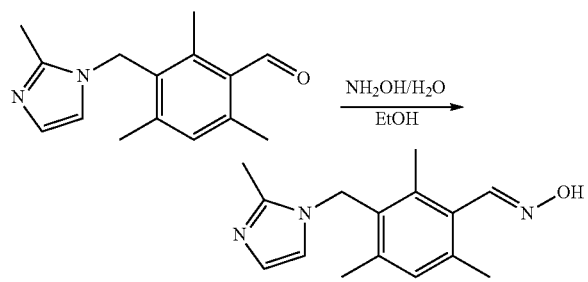

An aqueous hydroxylamine solution (809 g, 0.134 mol, 50% in water, Aldrich) in EtOH (10 ml) is added to a solution of 2,4,6-trimethyl-3-((2-methyl-1H-imidazol-1-yl)methyl)benzaldehyde (20.3 g, 0.084 mol) in EtOH (110 ml) at 40° C. The reaction medium is stirred at a temperature of 50 to 55° C. for 2.5 hours. After returning to 23° C., the precipitate obtained is filtered off, washed twice on the filter with an EtOH/H₂O (10 ml/15 ml) mixture and dried under atmospheric pressure at ambient temperature for 15 to 20 hours. A white solid (19.57 g, yield 91%) with a melting point of 247° C. is obtained. The molar purity is greater than 87% (¹H NMR).

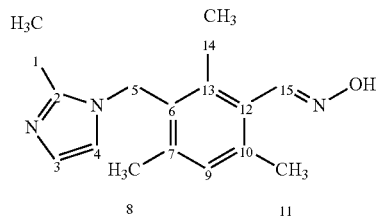

| No. | δ ¹H (ppm) | δ ¹³C (ppm) |
|---|---|---|
| 1 | 2.31 | 12.7 |
| 2 | — | 143.4 |
| 3 | 6.58 | 125.8 |
| 4 | 6.22 | 116.9 |
| 5 | 4.97 | 43.2 |
| 6 | — | 129.3 |
| 7 | — | 136.2 |
| 8 | 2.23 | 20.2 |
| 9 | 6.97 | 130 |
| 10 | — | 137.3 |
| 11 | 2.15 | 19.1 |
| 12 | — | 129.1 |
| 13 | — | 136.1 |
| 14 | 2.11 | 15.9 |
| 15 | 8.25 | 147.4 |
| OH | 11.11 | — |

II.2-5—Synthesis of 2,4,6-trimethyl-3-((2-methyl-1H-imidazol-1-yl)methyl)benzonitrile Oxide

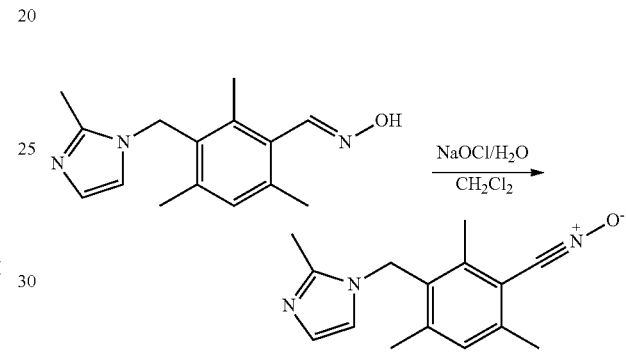

An aqueous solution of NaOCl (4% of active chlorine, Aldrich, 49 ml) is added dropwise over 5 minutes to a mixture of 2,4,6-trimethyl-3-((2-methyl-1H-imidazol-1-yl)methyl)benzaldehyde oxime (8.80 g, 0.034 mol) in CH₂Cl₂ (280 ml) at 6° C. The temperature of the reaction medium is maintained between 6° C. and 8° C. The reaction medium is subsequently stirred at 8° C. to 21° C. for 2 hours. The organic phase is separated. The organic phase is washed with water (3 times with 50 ml). After concentrating under reduced pressure (temperature of the bath=22-23° C., 220 mbar), petroleum ether (10 ml) is added, the solvent is evaporated down to 8-10 ml and the solution is maintained at −18° C. for 10-15 hours, so as to obtain a precipitate. The precipitate is filtered off, washed on the filter with the CH₂Cl₂/petroleum ether (2 ml/6 ml) mixture and then with petroleum ether (2 times 10 ml), and finally dried under atmospheric pressure at ambient temperature for 10-15 hours. A white solid (5.31 g, yield 61%) with a melting point of 139° C. is obtained. The molar purity is greater than 95 mol % (¹H NMR).

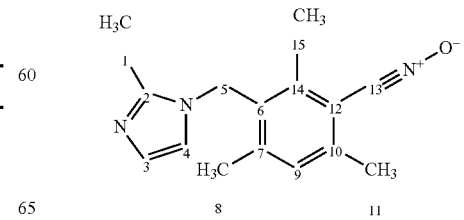

| No. | δ ¹H (ppm) | δ ¹³C (ppm) |
|---|---|---|
| 1 | 2.3 | 12.6 |
| 2 | — | 143.6 |
| 3 | 6.59 | 126.1 |
| 4 | 6.27 | 117.1 |
| 5 | 4.99 | 43 |
| 6 | — | 130.6 |
| 7 | — | 140.7 |
| 8 | 2.16 | 19.2 |
| 9 | 7.12 | 129.9 |
| 10 | — | 141 |
| 11 | 2.34 | 20 |
| 12 | — | 112.1 |
| 13 | — | NI |
| 14 | — | 140.8 |
| 15 | 2.28 | 17.7 |

II.3-Grafting of the 1,3-dipolar Compound 2,4,6-trimethyl-3-((2-methyl-1H-imidazol-1-yl)methyl)benzonitrile Oxide Use is made of the modifying agent obtained according to the procedure described above with a molar purity of 93 mol %.

The SBR before modification contains 25% of styrene units and 58% of 1,2-units of the butadiene part.

The 2,4,6-trimethyl-3-((2-methyl-1H-imidazol-1-yl)methyl)benzonitrile oxide (0.58 g, 2.26 mmol) is incorporated in 50 g of SBR on an open mill (external mixer at 30° C.). 0.5 g of antioxidant N-(1,3-dimethylbutyl)-N'-phenyl-p-phenylenediamine is subsequently incorporated. The mixture is homogenized in 15 turnover passes.

This compounding phase is followed by a heat treatment at 120° C. for 10 minutes under a press at a pressure of 10 bar.

Analysis by ¹H NMR made it possible to determine a molar degree of grafting of 0.23% and a molar grafting yield of 83%.

The quantification of the functional group by NMR is carried out by integrating an Hb proton of the unit below:

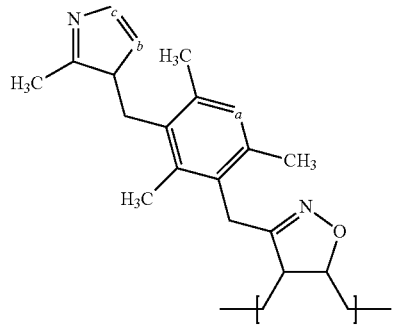

CH (b) located at 6.25 ppm relating to the SBR matrices

II.4—Synthesis of the 1,3-dipolar Compound 2,4,6-trimethyl-3-((2-methyl-1H-benzo[d]imidazol-1-yl)methyl)benzonitrile Oxide II.4-1—Synthesis of 2-(chloromethyl)-1,3,5-trimethylbenzene The synthesis is identical to that described in section II.2-1.

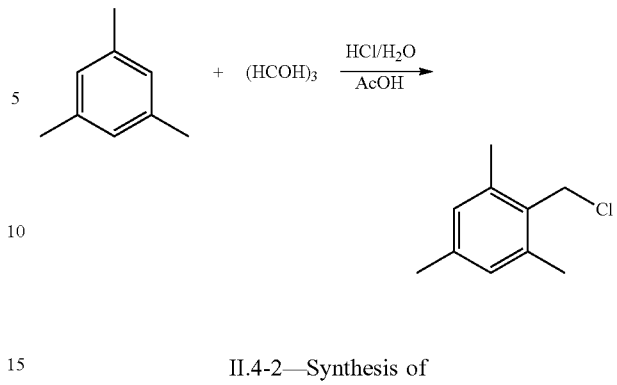

II.4-2—Synthesis of 3-(chloromethyl)-2,4,6-trimethylbenzaldehyde

The synthesis is identical to that described in section II.2-2.

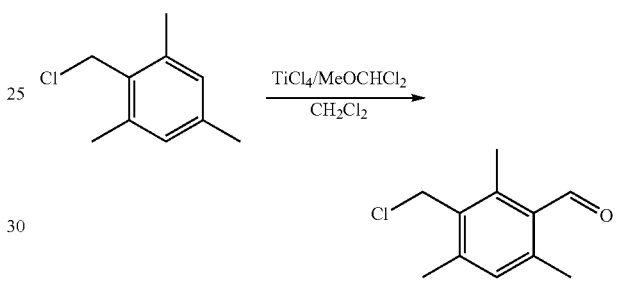

II.4-3—Synthesis of 2,4,6-trimethyl-3-((2-methyl-1H-benzo[d]imidazol-1-yl)methyl)benzaldehyde

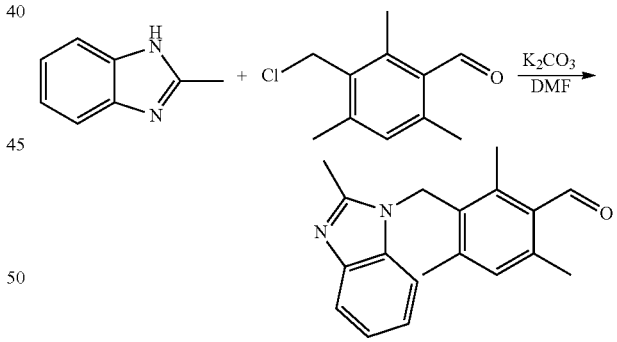

A mixture of aldehyde (11.9 g, 60.5 mmol), 2-methyl-benzimidazole (8.00 g, 60.5 mmol) and potassium carbonate (6.27 g, 45.4 mmol) in DMF (dimethylformamide, 15 ml) is stirred at 80° C. for one hour and at 90° C. for three hours. The mixture is subsequently diluted with water (600 ml). The organic phase is extracted with EtOAc (3 times 150 ml) and washed with water (4 times 75 ml). The solvents are evaporated under reduced pressure (36° C. ($T_{bath}$)) to result in a brown oil. The latter is crystallized from petroleum ether 40/60 (15 ml) and ethyl acetate (20 ml).

A solid (11.70 g, 40.0 mmol, yield 66%) with a melting point of 118° C. is obtained. The molar purity is 70%, EtOAc—5% (¹H NMR).

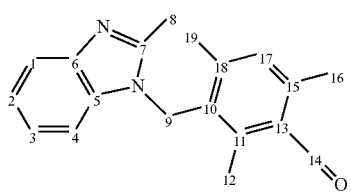

| Solvent: DMSO | | |
|---|---|---|
| No. | δ $^1$H (ppm) | δ $^{13}$C (ppm) |
| 1 | 7.45 | 118.0 |
| 2 | 7.01 | 120.5 |
| 3 | 6.93 | 121.2 |
| 4 | 6.79 | 109.6 |
| 5 | / | 134.9 |
| 6 | / | 142.1 |
| 7 | / | 151.8 |
| 8 | 2.38 | 14.1 |
| 9 | 5.42 | 42.6 |
| 10 | / | ~131 |
| 11 | / | 139.4 |
| 12 | 2.28 | 15.1 |
| 13 | / | 131.7 |
| 14 | 10.44 | 194.3 |
| 15 | / | 142.4 |
| 16 | ~2.44 | 19.8 |
| 17 | 7.04 | 131.2 |
| 18 | / | ~141.8 |
| 19 | 2.18 | 20.3 |

II.4—Synthesis of 2,4,6-trimethyl-3-((2-methyl-1H-benzo[d]imidazol-1-yl)methyl)benzaldehydeoxime

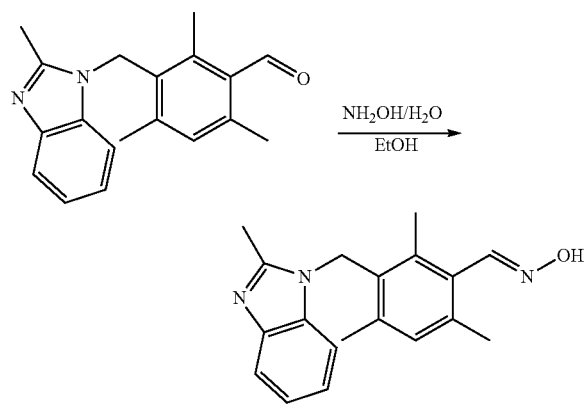

A hydroxylamine solution (6.14 g, 62.9 mmol, 50% in water, Aldrich) in EtOH (20 ml) is added to a solution of aldehyde (11.5 g, 39.4 mmol) in EtOH (80 ml) at 35° C. The reaction medium is stirred at 48-50° C. for 3.5 hours. The reaction medium is subsequently cooled down to 10-15° C. and the precipitate obtained is filtered off, washed on the filter with a mixture of ethanol and water (twice with 5 ml and 10 ml mixture) and then dried under atmospheric pressure at ambient temperature for 15-20 hours.

A solid (7.95 g, 25.9 mmol, yield 66%) with a melting point of 248° C. is obtained. The molar purity is greater than 80% ($^1$H NMR).

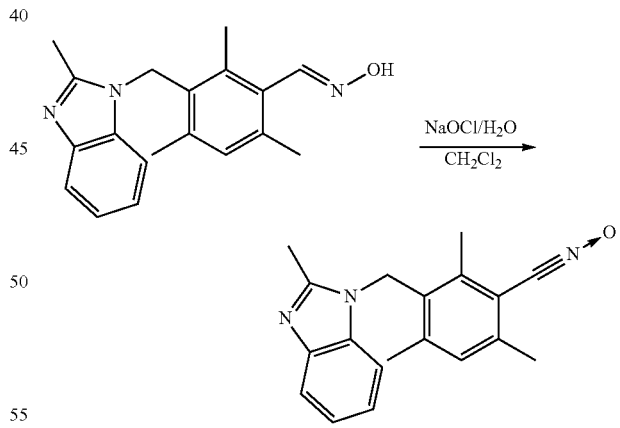

| No. | δ $^1$H (ppm) | δ $^{13}$C (ppm) |
|---|---|---|
| 1 | 7.43 | 117.8 |
| 2 | 7.01 | 120.3 |
| 3 | 6.91 | 121 |
| 4 | 6.78 | 109.6 |
| 5 | / | 134.9 |
| 6 | / | 142 |
| 7 | / | 151.7 |
| 8 | 2.37 | 14 |
| 9 | 5.37 | 43.1 |
| 10/11/13/18 | / | between 129.3 and 136.2 |
| 12 | 2.06 | 16.3 |
| 14 | 8.24 | 147.3 |
| 15 | / | 137.1 |
| 16 | 2.23 | 20.3 |
| 17 | 6.96 | 130.1 |
| 19 | 2.12 | 19.6 |

II.4-5—Synthesis of 2,4,6-trimethyl-3-((2-methyl-1H-benzo[d]imidazol-1-yl)methyl)benzonitrileoxide An aqueous solution of NaOCl (6% of active chlorine) (25.4 ml) is added dropwise over 6-8 minutes to a solution of oxime (6.20 g, 20.2 mmol) in dichloromethane (150 ml) cooled down to 5° C. The reaction medium is stirred for 4.5 hours until an emulsion is formed at 10° C. The organic phase is separated and washed with water (3 times with 25 ml). After evaporation of the solvent under reduced pressure ($T_{bath}$ 22-23° C.) until crystallization occurs, petroleum ether (40/60) (10 ml) and dichloromethane (4 ml) are added. The suspension is stirred for 10-15 minutes and the precipitate is filtered off, washed on the filter with the CH$_2$Cl$_2$/petroleum ether (2 ml/4 ml) mixture and with petroleum ether (40/60) (6 ml), and finally dried under atmospheric pressure at ambient temperature for 10-15 hours.

A white solid (4.85 g, 15.9 mmol, yield 79%) with a melting point of 142° C. is obtained. The molar purity is greater than 71% ($^1$H NMR).

The crude product (4.4 g) is redissolved in acetone (100 ml), this solution is then poured into water (500 ml) and the suspension is stirred for 5-10 minutes. The precipitate is filtered off, washed on the filter with water (200 ml) and dried under atmospheric pressure at ambient temperature for 10-15 hours.

A white solid (3.82 g, 12.6 mmol, yield 62%) with a melting point of 136.5-137.5° C. is obtained with a purity of 94 mol % by $^1$H NMR.

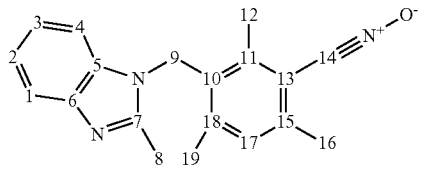

| No. | δ $^1$H (ppm) | δ $^{13}$C (ppm) |
|---|---|---|
| 1 | 7.45 | 118.2 |
| 2 | 7.02 | 120.7 |
| 3 | 6.95 | 121.2 |
| 4 | 6.81 | 109.6 |
| 5 | / | 134.7 |
| 6 | / | 141.9 |
| 7 | / | 151.7 |
| 8 | 2.36 | 13.9 |
| 9 | 5.39 | 42.8 |
| 10 | / | 130.5 |
| 11 | / | between 140.2 and 140.6 |
| 12 | 2.24 | 18.0 |
| 13 | / | 112.3 |
| 14 | / | Undetected |
| 15 | / | 140.9 |
| 16 | 2.34 | 19.9 |
| 17 | / | 130.2 |
| 18 | / | between 140.2 and 140.6 |
| 19 | 2.1 | 19.7 |

Solvent: DMSO

II.5—Grafting of the 1,3-dipolar Compound 2,4,6-trimethyl-3-(2-methyl-1H-benzo[d]imidazol-1-yl)methyl)benzonitrile Oxide A grafted isoprene unit is represented in the figure below:

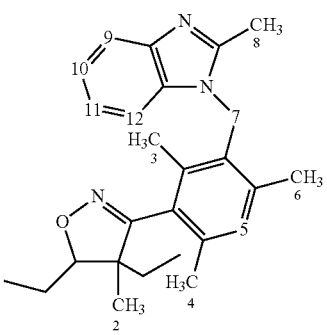

Use is made of the 1,3-dipolar compound obtained according to the procedure described in section II.4.

The synthetic polyisoprene (IR) before modification contains 98% by weight of cis-1,4-units.

The 1,3-dipolar compound is incorporated in a proportion of 1.35 g per 100 g of IR on an open mill (external mixer at 30° C.). 1 g of antioxidant N-(1,3-dimethylbutyl)-N'-phenyl-p-phenylenediamine is subsequently incorporated per 100 g of IR. The mixture is homogenized in 12 turnover passes.

This compounding phase is followed by a heat treatment at 120° C. for 10 minutes under a press at a pressure of 10 bar.

Analysis by $^1$H NMR made it possible to determine a molar degree of grafting of 0.20% and a molar grafting yield of 71%.

II.6—Synthesis of the 1,3-dipolar Compound N-(4-((1H-imidazol-1-yl)methyl)benzylidene)aniline Oxide (Va)

This compound can be prepared according to the following reaction scheme:

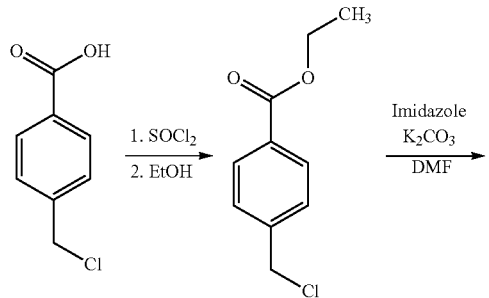

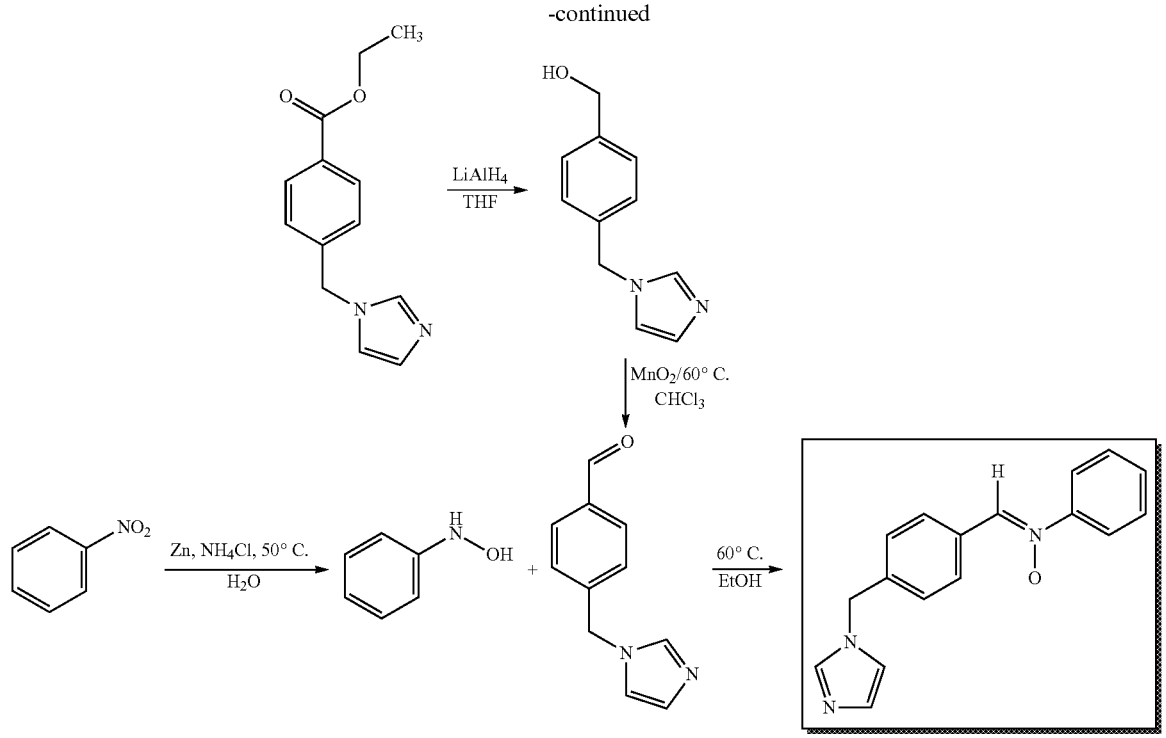

II.6-1—Synthesis of Ethyl 4-(chloromethyl)benzoate

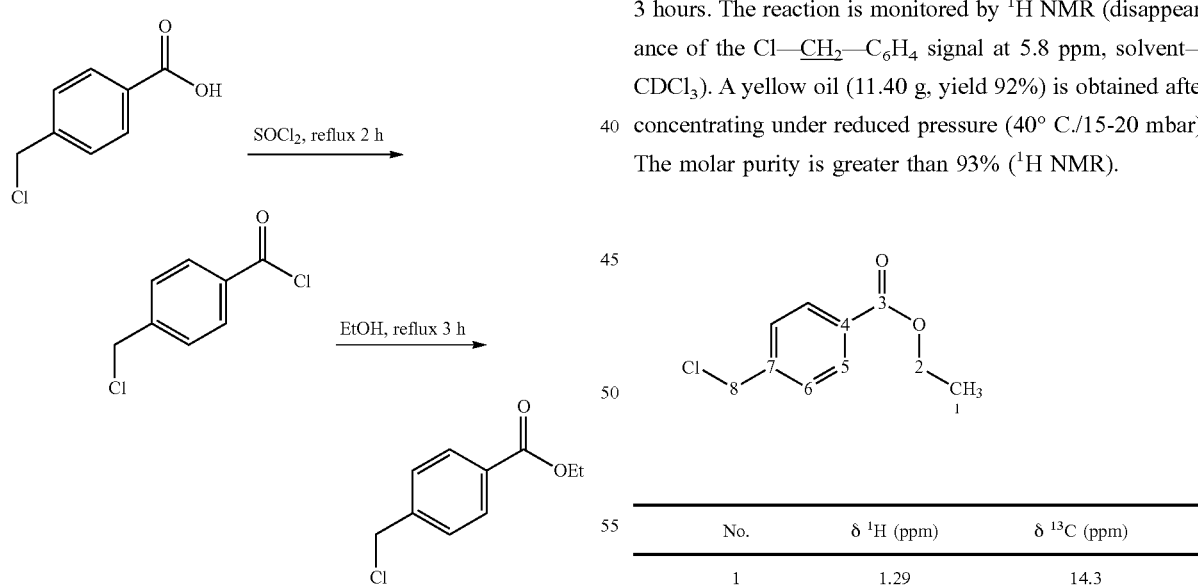

A mixture of 4-chloromethylbenzoic acid (10.64 g, 0.062 mol), DMF (70 mg, catalytic amount) and SOCl$_2$ (25 ml, 0.346 mol) is heated at 75° C. for 2 hours. The brown solution is evaporated under reduced pressure at 30° C. for 1.5 hours. 12.9 g of a brown oil containing a small amount of a solid are obtained. After filtration, anhydrous ethanol (60 ml) is added all at once. The temperature of the reaction medium immediately rises up to 40° C. The solution obtained is subsequently brought to reflux (T$_{bath}$ 95° C.) for 3 hours. The reaction is monitored by $^1$H NMR (disappearance of the Cl—$\underline{CH_2}$—C$_6$H$_4$ signal at 5.8 ppm, solvent—CDCl$_3$). A yellow oil (11.40 g, yield 92%) is obtained after concentrating under reduced pressure (40° C./15-20 mbar). The molar purity is greater than 93% ($^1$H NMR).

| No. | δ $^1$H (ppm) | δ $^{13}$C (ppm) |
|---|---|---|
| 1 | 1.29 | 14.3 |
| 2 | 4.28 | 61.2 |
| 3 | / | 165.8 |
| 4 | / | 130.9 |
| 5 | 7.95 | 130.1 |
| 6 | 7.48 | 129.2 |
| 7 | / | 143.2 |
| 8 | 4.68 | 45.7 |

Solvent: d$_6$-acetone

II.6-2—Synthesis of Ethyl 4-((1H-imidazol-1-yl)methyl)benzoate

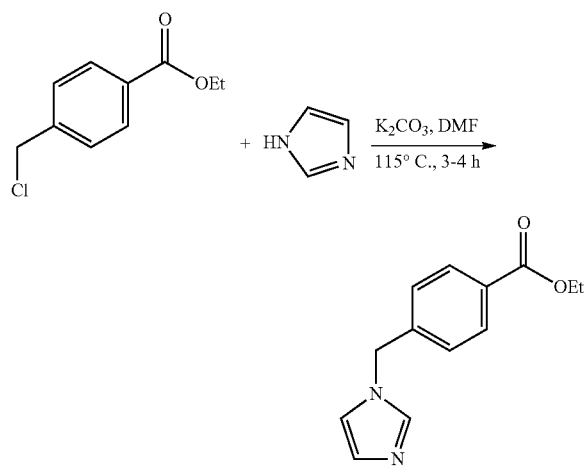

A mixture of ethyl 4-(chloromethyl)benzoate (13.55 g, 0.068 mol), imidazole (4.62 g, 0.068 mol) and $K_2CO_3$ (12.48 g, 0.090 mol) in DMF (100 ml) is heated at 115° C. ($T_{bath}$) for 3-4 hours. After cooling under an inert atmosphere (nitrogen), the reaction medium is maintained at ambient temperature for 10-12 hours. The yellow precipitate formed is filtered off and washed twice with DMF (30 ml). Concentrating the solvent under reduced pressure at 70-80° C. makes it possible to obtain approximately 22 g of brown oil which contains DMF.

The crude reaction product is dissolved in $CH_2Cl_2$ (150 ml) and then concentrated under reduced pressure at 70-80° C. The organic phase is extracted three times with $CH_2Cl_2$ and the combined organic phases are washed with water. A brown oil (8.00 g, yield 51%) is obtained. The molar purity is greater than 81% ($^1$H NMR). The product was used without additional purification.

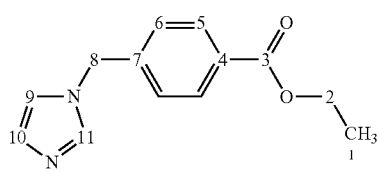

| No. | δ $^1$H (ppm) | δ $^{13}$C (ppm) |
| --- | --- | --- |
| 1 | 1.28 | 14.4 |
| 2 | 4.27 | 61.2 |
| 3 | — | 165.9 |
| 4 | — | 129.1(?) |
| 5 | 7.92 | 130.3 |
| 6 | 7.29 | 127.9 |
| 7 | — | 143.5 |
| 8 | 5.29 | 50.1 |
| 9 | 7.05 | 119.6 |
| 10 | 6.89 | 129.7 |
| 11 | 7.63 | 129.4 |

II.6-3—Synthesis of 4-((1H-imidazol-1-yl)methyl)phenylmethanol

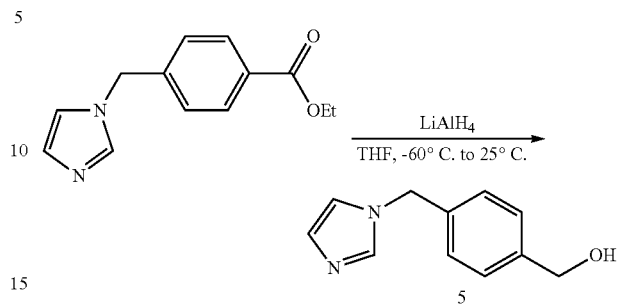

A solution of $LiAlH_4$ (1.50 g, 0.039 mol) in anhydrous THF (230 ml) is cooled to −60° C. A solution of ethyl 4-((1H-imidazol-1-yl)methyl)benzoate (7.80 g, 0.028 mol, 81 mol %) in anhydrous THF (100 ml) is added under argon over 15 minutes. The reaction medium is stirred at −60° C. for 1 hour and then at ambient temperature for 10-12 hours. Water (20 ml) is added dropwise (an exothermic reaction). The precipitate formed is filtered off and the filtrate is concentrated under reduced pressure. The crude product obtained is dissolved in $CH_2Cl_2$ (100 ml) in order to precipitate insoluble materials. After filtering and concentrating under reduced pressure, a yellow oil (4.96 g, yield 93%) is obtained. The molar purity is greater than 85% ($^1$H NMR).

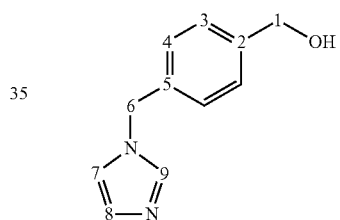

| No. | δ $^1$H (ppm) | δ $^{13}$C (ppm) |
| --- | --- | --- |
| 1 | 4.45 | 62.5 |
| 2 | / | 141.8 |
| 3 | 7.26 | ~126.6 |
| 4 | 7.17 | 127.0 |
| 5 | / | 139.7 |
| 6 | 5.10 | 49.2 |
| 7 | 7.10 | 119.0 |
| 8 | 6.87 | 128.1 |
| 9 | 7.70 | 136.8 |

Solvent: $d_6$-DMSO

II.6-4—Synthesis of 4-((1H-imidazol-1-yl)methyl)benzaldehyde

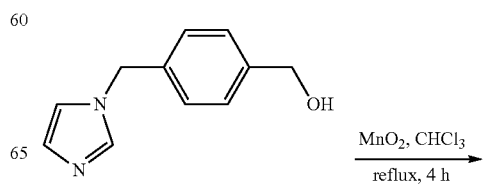

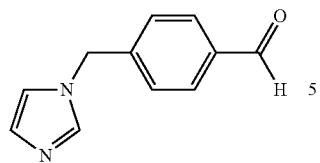

A mixture of MnO₂ (6.88 g, 0.079 mol) and 4-((1H-imidazol-1-yl)methyl)phenylmethanol (4.57 g, 0.021 mol, 85 mol % by ¹H NMR) in CHCl₃ (180 ml) is stirred at reflux temperature for 4 hours. The reaction medium is cooled down to ambient temperature and is kept stirred at this temperature for 10-12 hours. The insoluble products are filtered off and the filtrate is concentrated under reduced pressure. A yellow oil (3.78 g, yield 98%) is obtained after concentrating under reduced pressure. The molar purity is greater than 81% (¹H NMR).

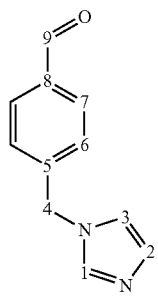

| No. | δ ¹H (ppm) | δ ¹³C (ppm) |
| --- | --- | --- |
| 1 | 7.37 | 136.8 |
| 2 | 6.88 | 129.1 |
| 3 | 6.74 | 118.6 |
| 4 | 5.02 | 49.4 |
| 5 | / | 142.4 |
| 6 | 7.07 | 126.7 |
| 7 | 7.62 | 129.4 |
| 8 | / | 135.2 |
| 9 | 9.74 | 190.7 |

Solvent: CDCl₃

II.6-5—Synthesis of Phenylhydroxylamine

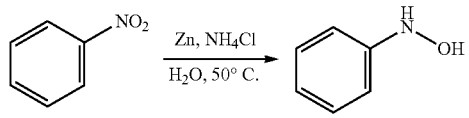 [SMILES: O=[N+]([O-])c1ccccc1 ; ONc1ccccc1]

Phenylhydroxylamine was synthesized according to the procedure described in Org. Syntheses Coll. Vol. 1, p. 445, 1941; Org. Syntheses Coll. Vol. 3, p. 668, 1955.

II.6-6—Synthesis of N-(4-((1H-imidazol-1-yl)methyl)benzylidene)aniline Oxide

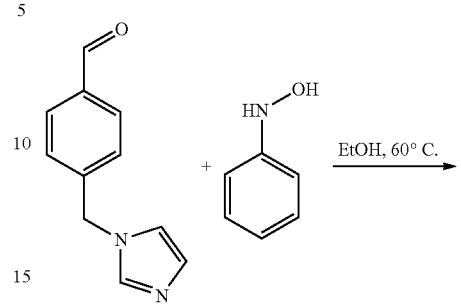

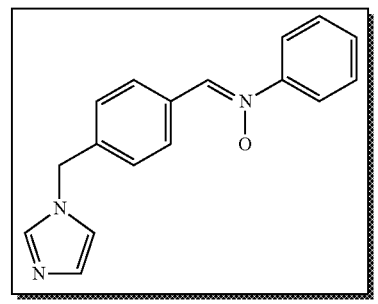

A solution of the aldehyde (3.48 g, 0.015 mol, 81 mol % by ¹H NMR) and phenylhydroxylamine (2.86 g, 0.026 mol) in anhydrous ethanol (20 ml) is stirred at 60° C. (T$_{bath}$) for 2 hours and subsequently at ambient temperature for 12 hours. The yellow precipitate is filtered off (0.249 g, containing the expected product). Water (30 ml) is added to the filtrate with vigorous stirring. The yellow precipitate then formed is filtered off after stirring for 20 minutes and is washed with a mixture of EtOH (10 ml) and water (20 ml) and then with water (50 ml). The two portions of solid are combined and dried under atmospheric pressure at ambient temperature for 10-12 hours. A yellow solid (3.71 g, yield 89%) with a molar purity of greater than 82% (¹H NMR) is obtained. An additional purification is applied by stirring at ambient temperature for 1.5 hours, filtering, washing on the filter with 50 ml of ethyl ether and drying at ambient temperature for 2 days.

A yellow solid (3.04 g, yield 78%) with a melting point of 115-116° C. is obtained. The molar purity is greater than 88% (¹H NMR).

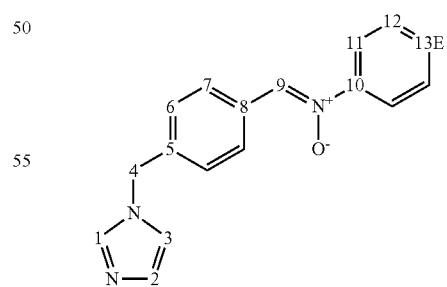

| No. | δ ¹H (ppm) | δ ¹³C (ppm) |
| --- | --- | --- |
| 1 | 7.72 | 137.3 |
| 2 | 6.87 | 128.5 |

-continued

| No. | δ ¹H (ppm) | δ ¹³C (ppm) |
|---|---|---|
| 3 | 7.15 | 119.4 |
| 4 | 5.2 | 50 |
| 5 | / | 139.9 |
| 6 | 7.3 | 127.1 |
| 7 | 8.4 | 128.8 |
| 8 | / | 130.3 |
| 9 | 8.44 | 132.8 |
| 10 | / | 148.1 |
| 11 | 7.84 | 121.2 |
| 12 | ~7.48 | 128.9 |
| 13 | | 129.7 |

Solvent: $d_6$-DMSO

II.7-Preparation of the Rubber Compositions

The g-SBR and g-IR elastomers are used in the preparation of the rubber compositions g-SBR-C and g-IR-C. The SBR and IR elastomers which were used to prepare the grafted g-SBR and g-IR elastomers are used in the unmodified form in order to constitute the elastomer matrix of the control compositions SBR-C and IR-C respectively.

The formulations (in phr) of the compositions are described in Table (I). The compositions g-SBR-C and g-IR-C are in accordance with the invention. The compositions SBR-C and IR-C are respective control compositions of the compositions g-SBR-C and g-IR-C.

These compositions are manufactured in the following way: the elastomer, the silica, the coupling agent and also the various other ingredients, with the exception of the vulcanization system, are successively introduced into an internal mixer (final degree of filling: approximately 70% by volume), the initial vessel temperature of which is approximately 110° C. Thermomechanical working (non-productive phase) is then carried out in one stage, which lasts approximately 5 min to 6 min, until a maximum "dropping" temperature of 160° C. is reached. The mixture thus obtained is recovered and cooled and then sulphur and an accelerator of sulphenamide type are incorporated on a mixer (homofinisher) at 23° C., everything being mixed (productive phase) for an appropriate time (for example between 5 and 12 min).

TABLE (I)

| Composition | SBR-C not in accordance | g-SBR-C in accordance | IR-C not in accordance | g-IR-C in accordance |
|---|---|---|---|---|
| SBR (1) | 100 | — | — | — |
| g-SBR (2) | — | 101 | — | — |
| IR (3) | — | — | 100 | — |
| g-IR (4) | — | — | — | 101 |
| Carbon black N234 | 3 | 3 | 3 | 3 |
| Silica (5) | 55 | 55 | 55 | 55 |
| Silane (6) | 5.5 | 5.5 | 5.5 | 5.5 |
| Antioxidant (7) | 1.5 | 1.5 | 1 | 1 |
| Antioxidant (8) | 1 | — | 1.5 | 0.5 |
| Antiozone wax | 1 | 1 | 1 | 1 |
| ZnO | 2.7 | 2.7 | 2.7 | 2.7 |
| Stearic acid | 2.5 | 2.5 | 2.5 | 2.5 |
| Sulphenamide (9) | 1.8 | 1.8 | 2 | 2 |
| Sulphur | 1.5 | 1.5 | 1.3 | 1.3 |

(1) SBR: SBR with 25% of styrene units and 56% of 1,2-units of the butadiene part
(2) g-SBR: SBR modified according to the synthesis described above in the preceding section II-3.
(3) IR: polyisoprene comprising 98% by weight of cis-1,4-units
(4) g-IR: IR modified according to the synthesis described above in the preceding section II-5.
(5) silica: Zeosil 1165 MP from Rhodia (HDS type)
(6) TESPT (Si69 from Degussa)
(7) 2,2,4-trimethyl-1,2-dihydroquinoline
(8) N-(1,3-dimethylbutyl)-N'-phenyl-p-phenylenediamine from Flexsys
(9) N-cyclohexyl-2-benzothiazolesulphenamide (Santocure CBS from Flexsys)

The compositions thus obtained are subsequently calendered, either in the form of plaques (with a thickness ranging from 2 to 3 mm) or thin sheets of rubber, for the measurement of their physical or mechanical properties, or in the form of profiled elements which can be used directly, after cutting and/or assembling to the desired dimensions, for example as semi-finished products for tyres, in particular for treads.

The crosslinking is carried out at 150° C. The crosslinking time, $t'_c(90)$, is the time necessary for the torque of the composition to reach 90% of the maximum torque of the composition. The torques of the composition are measured at 150° C. with an oscillating disc rheometer, according to Standard DIN 53529—Part 3 (June 1983). $t'_c(90)$ is determined according to Standard NF T 43-015 for each of the compositions.

II.8—Characterization Tests—Results

Tensile Tests:

These tensile tests make it possible to determine the elasticity stresses. Unless otherwise indicated, they are carried out in accordance with French Standard NF T 46-002 of September 1988. Processing the tensile recordings also makes it possible to plot the curve of modulus as a function of the elongation. At first elongation, the nominal secant modulus, calculated by reducing to the initial cross-section of the test specimen, (or apparent stress, in MPa) is measured at 100% elongation, denoted ASM100.

All these tensile measurements are carried out under the standard temperature conditions (23±2° C.) according to Standard NF T 46-002.

Dynamic Properties:

The dynamic properties are measured on a viscosity analyser (Metravib VA4000) according to Standard ASTM D 5992-96. The response of a sample of vulcanized composition (cylindrical test specimen with a thickness of 4 mm and a cross-section of 400 mm²), subjected to a simple alternating sinusoidal shear stress, at a frequency of 10 Hz, under standard temperature conditions (23° C.) according to Standard ASTM D 1349-99 or, as the case may be, at a different temperature (100° C.), is recorded. A strain amplitude sweep is carried out from 0.1% to 100% (outward cycle) and then from 100% to 0.1% (return cycle). The results made use of are the complex dynamic shear modulus (G*) at 25% strain, the loss factor tan(δ) and the difference in modulus (ΔG*) between the values at 0.1% and 100% strain (Payne effect). For the return cycle, the maximum value of tan(δ) observed, denoted tan(δ)max, is indicated.

The results are recorded in Table (II) below.

TABLE (II)

| Properties in the cured state | Composition | | | |
|---|---|---|---|---|
| | SBR-C | g-SBR-C | IR-C | g-IR-C |
| ASM100 at 23° C. | 2.83 | 3.19 | 1.84 | 3.72 |
| tan(δ)max at 23° C. | 0.28 | 0.17 | 0.23 | 0.08 |
| ΔG* at 23° C. | 4 | 0.93 | 3.27 | 0.59 |
| G* at 100° C. | 1.61 | 1.63 | 1.35 | 1.45 |
| tan(δ)max at 100° C. | 0.13 | 0.08 | 0.13 | 0.06 |

The compositions g-SBR-C and g-IR-C exhibit, at 23° C., a modulus ASM100 at 23° C. which is much greater than that of the respective control compositions SBR-C and IR-C. This increase in stiffness in the cured state is obtained although a very significant decrease in the hysteresis at 23° C. is also observed for g-SBR-C and g-IR-C, in comparison with their respective controls SBR-C and IR-C. The increase in the stiffness in the cured state is all the more remarkable as the fall in hysteresis is very strong.

As good road behaviour of a tyre is generally associated with a high stiffness in the cured state of the composition which constitutes its tread, this result foretells good road behaviour of a tyre having a tread comprising a g-SBR-C or g-IR-C composition.

Furthermore, it is observed that the compositions according to the invention g-SBR-C and g-IR-C retain a level of stiffness in the cured state at 100° C. comparable to that of the respective control compositions SBR-C and IR-C. These results presage a temperature versatility of the rubber composition in accordance with the invention. This is because it may be expected that a tread containing the composition g-SBR-C or g-IR-C will make it possible for the tyre to have a road behaviour at least just as good as would be had by the control composition SBR-C or IR-C, during more extreme rolling conditions, in particular for sports car tyres rolling at high-speed.

The invention claimed is:

1. A process for modifying, by a grafting reaction, an unsaturated polymer which exhibits at least one unsaturation, the process comprising reacting a 1,3-dipolar compound with the at least one unsaturation of the unsaturated polymer,
wherein the 1,3-dipolar compound is of formula (I):

Q-A-B      (I), wherein Q comprises a dipole containing at least one nitrogen atom,
wherein A is an atom or a group of atoms connecting Q to B, and
wherein B comprises a ring of formula (II):

$$\begin{array}{c}\text{(II)}\end{array}$$

wherein three of four symbols Z, Y, R, and R' are identical or different, each representing an atom or a group of atoms, it being possible for Z and Y to form, together with carbon atoms to which they are attached, a ring, and a fourth of the four symbols Z, Y, R, and R' denotes a direct attachment to A.

2. The process according to claim 1, wherein R' denotes a direct attachment to A.

3. The process according to claim 2, wherein Z and Y are each a hydrogen atom.

4. The process according to claim 2, wherein Z and Y form the ring together with the carbon atoms to which they are attached.

5. The process according to claim 1, wherein R represents a hydrogen atom or a carbon-based group which can contain at least one heteroatom.

6. The process according to claim 5, wherein R is an alkyl group containing from 1 to 12 carbon atoms.

7. The process according to claim 1, wherein A is an aliphatic group or an aromatic group containing up to 20 carbon atoms which can contain at least one heteroatom.

8. The process according to claim 7, wherein A is an alkylene group containing from 1 to 20 carbon atoms or an arylene group.

9. The process according to claim 1, wherein the compound is selected from the group consisting of nitrile oxides, nitrile imines, and nitrones.

10. The process according to claim 9, wherein Q contains a —C≡N→O unit.

11. The process according to claim 10, wherein Q comprises a unit of formula (III):

$$\begin{array}{c}\text{(III)}\end{array}$$

wherein four of five symbols $R_1$ to $R_5$ are identical or different, each being an atom or a group of atoms, and a fifth of the five symbols $R_1$ to $R_5$ denotes a direct attachment to A, and
wherein neither of $R_1$ and $R_5$ is H.

12. The process according to claim 11, wherein $R_1$, $R_3$, and $R_5$ are each an alkyl group of 1 to 6 carbon atoms.

13. The process according to claim 12, wherein the compound is 2,4,6-trimethyl-3-((2-methyl-1H-imidazol-1-yl)methyl)benzonitrile oxide or 2,4,6-triethyl-3-((2-methyl-1H-imidazol-1-yl)methyl)benzonitrile oxide.

14. The process according to claim 9, wherein Q contains a —C=N(→O) unit.

15. The process according to claim 14, wherein Q comprises a unit of formula (IV) or (V):

$$Y_1-HC=N^{+}(O^{-})-Y_2 \quad \text{(IV)}$$

-continued

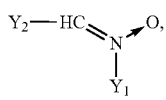
(V)

wherein $Y_1$ is an aromatic group containing from 6 to 20 carbon atoms or an aliphatic group, and wherein $Y_2$, comprising a direct attachment to A, is an aliphatic group or an aromatic group comprising, on its aromatic nucleus, the direct attachment to A.

16. The process according to claim 14, wherein the compound is of formula (IVa), (IVb), (Va), or (Vb):

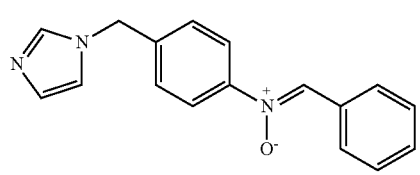
(IVa)

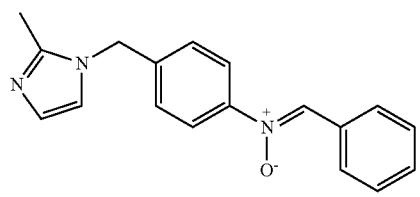
(IVb)

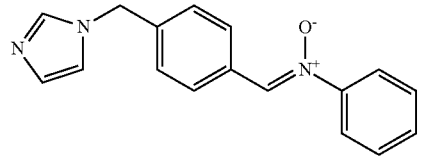
(Va)

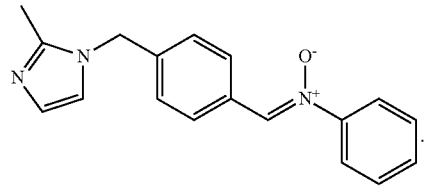
(Vb)

17. The process according to claim 1, wherein the 1,3-dipolar compound is reacted according to a stoichiometry of between 0 and 3 molar equivalents of imidazole ring per 100 moles of monomer units constituting the polymer.

18. The process according to claim 1, wherein the unsaturated polymer is a diene polymer.

19. The process according to claim 18, wherein the diene polymer is an essentially unsaturated diene elastomer selected from the group consisting of a polybutadiene, a polyisoprene, a butadiene copolymer, an isoprene copolymer, and a mixture thereof.

20. A polymer obtained by the process according to claim 1.

* * * * *